US011813115B2

(12) United States Patent
Jin et al.

(10) Patent No.: US 11,813,115 B2
(45) Date of Patent: Nov. 14, 2023

(54) PORTABLE ULTRASOUND APPARATUS, PORTABLE ULTRASOUND SYSTEM AND DIAGNOSING METHOD USING ULTRASOUND

(71) Applicant: SAMSUNG MEDISON CO., LTD., Gangwon-do (KR)

(72) Inventors: Gil-ju Jin, Gangwon-do (KR); Mi-jeoung Ahn, Gangwon-do (KR); Hyoung-jin Kim, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 108 days.

(21) Appl. No.: 17/021,269

(22) Filed: Sep. 15, 2020

(65) Prior Publication Data

US 2020/0405262 A1 Dec. 31, 2020

Related U.S. Application Data

(63) Continuation of application No. 14/060,282, filed on Oct. 22, 2013, now Pat. No. 10,799,212.

(30) Foreign Application Priority Data

Apr. 3, 2013 (KR) .......................... 10-2013-0036438

(51) Int. Cl.
*A61B 8/00* (2006.01)
(52) U.S. Cl.
CPC .......... *A61B 8/4427* (2013.01); *A61B 8/4444* (2013.01); *A61B 8/4477* (2013.01); *A61B 8/465* (2013.01); *A61B 8/464* (2013.01)

(58) Field of Classification Search
None
See application file for complete search history.

(56) References Cited

U.S. PATENT DOCUMENTS

| 5,014,710 A | 5/1991 | Maslak et al. |
| 5,552,645 A | 9/1996 | Weng |
| 5,722,412 A | 3/1998 | Pflugrath et al. |
| 5,782,769 A | 7/1998 | Hwang et al. |

(Continued)

FOREIGN PATENT DOCUMENTS

| JP | 2009-045458 A | 3/2009 |
| KR | 10-2009-0022723 A | 3/2009 |

(Continued)

OTHER PUBLICATIONS

Office Action issued in corresponding Korean Patent Application No. 10-2013-0036438 dated Jan. 30, 2020, with English translation.

(Continued)

*Primary Examiner* — Colin T. Sakamoto
(74) *Attorney, Agent, or Firm* — Morgan, Lewis & Bockius LLP

(57) ABSTRACT

Provided are a portable ultrasound apparatus, a portable ultrasound system, and an ultrasound diagnosis method performed by using the portable ultrasound apparatus. The portable ultrasound apparatus includes at least two probes having different specifications; a first display unit for displaying an ultrasound image; and a second display unit for displaying a control screen.

11 Claims, 9 Drawing Sheets

(56) References Cited

U.S. PATENT DOCUMENTS

| | | | |
|---|---|---|---|
| 6,261,249 B1* | 7/2001 | Talish | A61B 8/4227 |
| | | | 600/459 |
| 6,716,167 B1 | 4/2004 | Henderson et al. | |
| 7,688,306 B2 | 3/2010 | Wehrenberg et al. | |
| 3,043,221 A1 | 10/2011 | Marteau et al. | |
| 8,043,221 B2* | 10/2011 | Marteau | G01S 15/8909 |
| | | | 600/459 |
| 9,532,768 B2 | 1/2017 | Marteau et al. | |
| 2002/0173719 A1 | 11/2002 | Zhao et al. | |
| 2005/0228281 A1 | 10/2005 | Nefos | |
| 2006/0026535 A1 | 2/2006 | Hotelling et al. | |
| 2006/0058654 A1 | 3/2006 | Di Marco et al. | |
| 2007/0073148 A1 | 3/2007 | Kim | |
| 2008/0119731 A1 | 5/2008 | Becerra et al. | |
| 2008/0125655 A1* | 5/2008 | Song | A61B 8/462 |
| | | | 600/443 |
| 2009/0018441 A1 | 1/2009 | Willsie et al. | |
| 2009/0043203 A1 | 2/2009 | Pelissier et al. | |
| 2009/0043204 A1 | 2/2009 | Pelissier et al. | |
| 2009/0043205 A1 | 2/2009 | Pelissier et al. | |
| 2009/0062652 A1 | 3/2009 | Shin et al. | |
| 2009/0093719 A1 | 4/2009 | Pelissier et al. | |
| 2010/0048194 A1 | 2/2010 | Park et al. | |
| 2010/0048252 A1 | 2/2010 | Kang et al. | |
| 2010/0063398 A1 | 3/2010 | Halmann et al. | |
| 2010/0145195 A1 | 6/2010 | Hyun | |
| 2010/0286527 A1 | 11/2010 | Cannon et al. | |
| 2011/0043434 A1* | 2/2011 | Roncalez | A61B 5/7445 |
| | | | 345/3.1 |
| 2011/0163986 A1* | 7/2011 | Lee | H04M 1/72427 |
| | | | 345/173 |
| 2011/0245623 A1 | 10/2011 | Chutani et al. | |
| 2012/0108975 A1 | 5/2012 | Marteau et al. | |
| 2012/0220873 A1 | 8/2012 | Hyun | |
| 2013/0072800 A1 | 3/2013 | Lee | |
| 2013/0165796 A1 | 6/2013 | Tashiro | |

FOREIGN PATENT DOCUMENTS

| | | |
|---|---|---|
| KR | 10-2010-0050845 A | 5/2010 |
| KR | 10-2012-0046709 A | 5/2010 |
| KR | 10-2010-0065720 A | 6/2010 |
| KR | 10-1089746 B1 | 12/2011 |
| WO | 2013/001484 A1 | 1/2013 |

OTHER PUBLICATIONS

Office Action issued in corresponding Korean Patent Application No. 10-2013-0036438 dated Oct. 30, 2019, with English translation.

European Search Report issued in corresponding European Patent Application No. 13186992.7-1660 dated Jul. 22, 2014.

Notice of Allowance issued in corresponding U.S. Appl. No. 14/060,282 dated Jun. 10, 2020.

Office Action issued in corresponding U.S. Appl. No. 14/060,282 dated Nov. 25, 2019.

Final Office Action issued in corresponding U.S. Appl. No. 14/060,282 dated Nov. 30, 2018.

Office Action issued in corresponding U.S. Appl. No. 14/060,282 dated Apr. 10, 2018.

Final Office Action issued in corresponding U.S. Appl. No. 14/060,282 dated Nov. 17, 2017.

Office Action issued in corresponding U.S. Appl. No. 14/060,282 dated May 10, 2017.

Final Office Action issued in corresponding U.S. Appl. No. 14/060,282 dated Dec. 1, 2016.

Office Action issued in corresponding U.S. Appl. No. 14/060,282 dated Apr. 7, 2016.

Extended European Search Report dated Dec. 16, 2022 issued in European Patent Application No. 22194362.4.

* cited by examiner

PORTABLE ULTRASOUND APPARATUS, PORTABLE ULTRASOUND SYSTEM AND DIAGNOSING METHOD USING ULTRASOUND

CROSS-REFERENCE TO RELATED PATENT APPLICATION

This application is the continuation application of U.S. patent application Ser. No. 14/060,282 filed Oct. 22, 2013, which claims the benefit of Korean Patent Application No. 10-2013-0036438, filed on Apr. 3, 2013, in the Korean Intellectual Property Office, the disclosures of which are incorporated herein in their entirety by reference.

BACKGROUND OF THE INVENTION

1. Field of the Invention

The present invention relates to a method and apparatus for diagnosing a target object by using a portable ultrasound apparatus and a portable ultrasound system.

2. Description of the Related Art

An ultrasound diagnosis apparatus delivers an ultrasound signal (in general, equal to or greater than 20 kHz) to a predetermined internal part of a target object by using a probe, and obtains an image of the internal part of the target object by using information of a reflected echo signal. In particular, the ultrasound diagnosis apparatus is used for medical purposes including detection of foreign materials in the target object, damage measurement and observation, or the like. Compared to X-rays, the ultrasound diagnosis apparatus is stable, displays an image in real-time, and is safe without a risk of radioactivity, so that the ultrasound diagnosis apparatus is widely used with an image diagnosis apparatus.

An image that is obtained by using the ultrasound diagnosis apparatus (hereinafter, referred to as an 'ultrasound image') may be displayed on the ultrasound diagnosis apparatus or may be stored in a storage medium and then may be displayed on another image display apparatus. For example, the ultrasound image may be reduced and then may be displayed on a screen of a mobile phone, a portable electronic device, a personal digital assistant (PDA), a tablet personal computer (PC), or the like.

Since an ultrasound apparatus according to the related art is large and heavy, the ultrasound apparatus is mainly fixed and used in a specific place. However, in an emergency room or an operating room in which an ultrasound diagnosis is performed, the ultrasound apparatus has to be moved whenever required. In order to solve this problem, a small ultrasound apparatus has been developed but a weight of the small ultrasound apparatus is not light enough for easily portability. Thus, there is a demand for an ultrasound apparatus that may be portable and that may use various probes.

SUMMARY OF THE INVENTION

The present invention provides a portable ultrasound apparatus and a portable ultrasound system capable of diagnosing a target object without separately having various probes.

The present invention also provides a diagnosing method performed by using the portable ultrasound apparatus and the portable ultrasound system.

According to an aspect of the present invention, there is provided a portable ultrasound apparatus including at least two probes having different specifications; a first display unit for displaying an ultrasound image that is generated based on ultrasound data received by one of the at least two probes; and a second display unit for displaying a control screen so as to control at least one of the ultrasound data and the ultrasound image.

Each of the at least two probes may include a linear array-type transducer, a convex array-type transducer, or a phased array-type transducer.

Each of the specifications may include at least one of a frequency of an ultrasound signal to be transmitted by each of the at least two probes, a bandwidth of the ultrasound signal, a total number of channels of each of the at least two probes, and a resolution of each of the at least two probes.

The first display unit and the second display unit may receive a touch input by a user.

The portable ultrasound apparatus may further include at least one button that is matched with a function related to an ultrasound diagnosis.

The function may be matched with the at least one button according to a user input.

The portable ultrasound apparatus may further include a sensing unit for detecting an activated probe from among the at least two probes.

The sensing unit may include at least one of a gyro sensor, an acceleration sensor, and a tilt sensor.

The portable ultrasound apparatus may further include an activation display unit for displaying an activated probe from among the at least two probes.

The portable ultrasound apparatus may further include a power unit that supplies power to the at least two probes, the first display unit, and the second display unit, and that is charged by wireless electric power received from an external power source.

The portable ultrasound apparatus may further include a power unit that supplies wireless electric power received from an external power source to the at least two probes, the first display unit, and the second display unit.

The first display unit and the second display unit may rotate and may display the ultrasound image and the control screen, based on an activated probe from among the at least two probes.

The first display unit and the second display unit may adjust at least one of a position and a size of the ultrasound image and the control screen based on a user input, and then may display the ultrasound image and the control screen.

The first display unit may display the control screen that is displayed by the second display unit, based on a user input of transition of a displayed screen.

The first display unit may display the ultrasound image that is displayed by the first display unit, based on a user input of transition of a displayed screen.

The first display unit and the second display unit may detect a position on one display unit from among the first display unit and the second display unit, based on a user input of a corresponding position on the other display unit from among the first display unit and the second display unit.

According to another aspect of the present invention, there is provided an ultrasound diagnosis method performed by using a portable ultrasound apparatus including at least two probes having different specifications, the ultrasound diagnosis method including operations of displaying an ultrasound image on a first display unit, wherein the ultrasound image is generated based on ultrasound data received by one of the at least two probes; and displaying a control screen on a second display unit, wherein the control screen controls at least one of the ultrasound data and the ultrasound image.

According to another aspect of the present invention, there is provided a portable ultrasound system including at least two probes having different specifications; a digital beamformer for focusing an ultrasound signal transmitted or received by each of the at least two probes; a processor for generating ultrasound data based on the ultrasound signal; an image processing unit for generating an ultrasound image based on the ultrasound data; a first display unit for displaying the ultrasound image; and a second display unit for displaying a control screen so as to control at least one of the ultrasound data and the ultrasound image.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
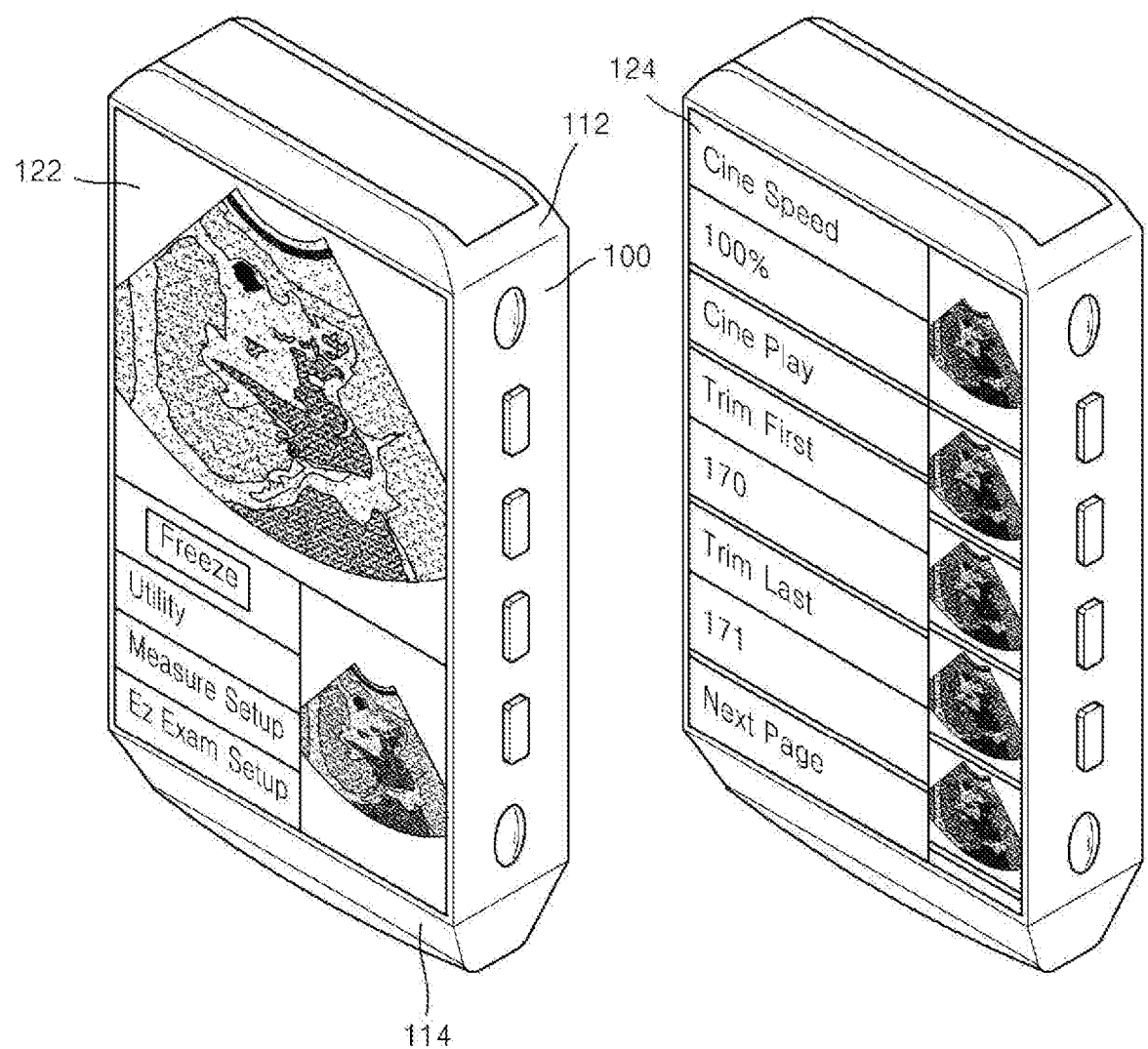
FIG. 1 is a perspective view illustrating a portable ultrasound apparatus according to an embodiment of the present invention.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

Hereinafter, the present invention will be described in detail by explaining exemplary embodiments of the invention with reference to the attached drawings in which reference numerals indicate structural elements.

Expressions such as "at least one of," when preceding a list of elements, modify the entire list of elements and do not modify the individual elements of the list.

FIG. 1 is a perspective view illustrating a portable ultrasound apparatus 100 according to an embodiment of the present invention. As illustrated in FIG. 1, the portable ultrasound apparatus 100 may include, but is not limited to, at least two probes 112 and 114, and at least two display units 122 and 124. That is, in another embodiment, the portable ultrasound apparatus 100 may include at least three probes and at least three display units. Also, positions or sizes of portions at which the probes 112 and 114 and the display units 122 and 124 are arranged are not limited to the present embodiment.

The portable ultrasound apparatus 100 sends an ultrasound signal to a target object via the probes 112 and 114, and obtains ultrasound data by analyzing an echo signal reflected from the target object. The probes 112 and 114 may have different specifications, for example, the probes 112 and 114 may be different from each other in an array form of transducers, a frequency of an ultrasound signal, or the like. Further, the portable ultrasound apparatus 100 may generate an ultrasound image from the ultrasound data and may display the ultrasound image on the display units 122 and 124.

Also, the portable ultrasound apparatus 100 may control at least one of the ultrasound data and the ultrasound image, based on a user input. That is, the portable ultrasound apparatus 100 may adjust a gain value of the ultrasound data or may adjust a power or a dynamic range of the ultrasound signal, based on the user input. Further, the portable ultrasound apparatus 100 may adjust the brightness, line density, colour, or the like of the ultrasound image, based on a user input.

In order to control at least one of the ultrasound data and the ultrasound image, the portable ultrasound apparatus 100 may display a control screen on the display units 122 and 124. In the embodiment of FIG. 1, the portable ultrasound apparatus 100 displays the ultrasound image on the display unit 122 and displays a control screen to display a moving picture of ultrasound images on the display unit 124. However, as will be described later with reference to FIG. 3, the portable ultrasound apparatus 100 may display various types of information as well as the ultrasound image and the control screen.

According to the present embodiment, the portable ultrasound apparatus 100 may diagnose the target object by using the probes 112 and 114 having different specifications, so that the portability and diagnosis efficiency in an ultrasound diagnosis may be improved.

Figure 2:
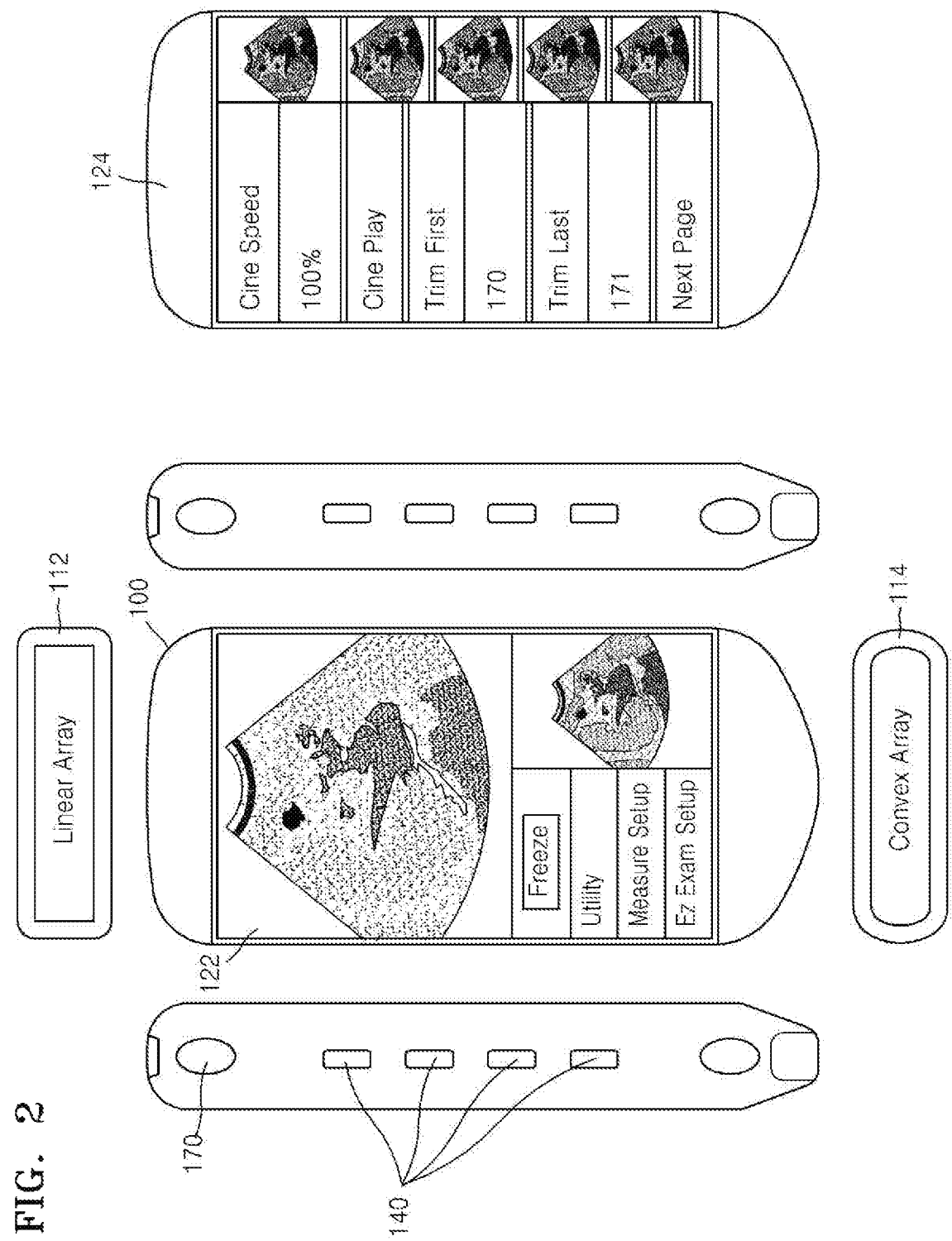
FIG. 2 illustrates six views of the portable ultrasound apparatus.

FIG. 2 illustrates six views of the portable ultrasound apparatus 100. In FIG. 2, a front view illustrates the display unit 122 that displays an ultrasound image, a left-side view and a right-side view of the portable ultrasound apparatus 100 illustrate a user input unit 140 including a plurality of buttons and an activation display unit 170, respectively. Also, a plane view and a bottom view of the portable ultrasound apparatus 100 illustrate the probe 112 (also referred to as the first probe 112) including a linear array-type transducer and the probe 114 (also referred to as the second probe 114) including a convex array-type transducer, respectively. A rear view of the portable ultrasound apparatus 100 illustrates the display unit 124 that displays a control screen.

However, a form and structure of the portable ultrasound apparatus 100 shown in FIGS. 1 and 2 may be changed, thus, the portable ultrasound apparatus 100 may include at least two probes and at least two display units.

Figure 3:
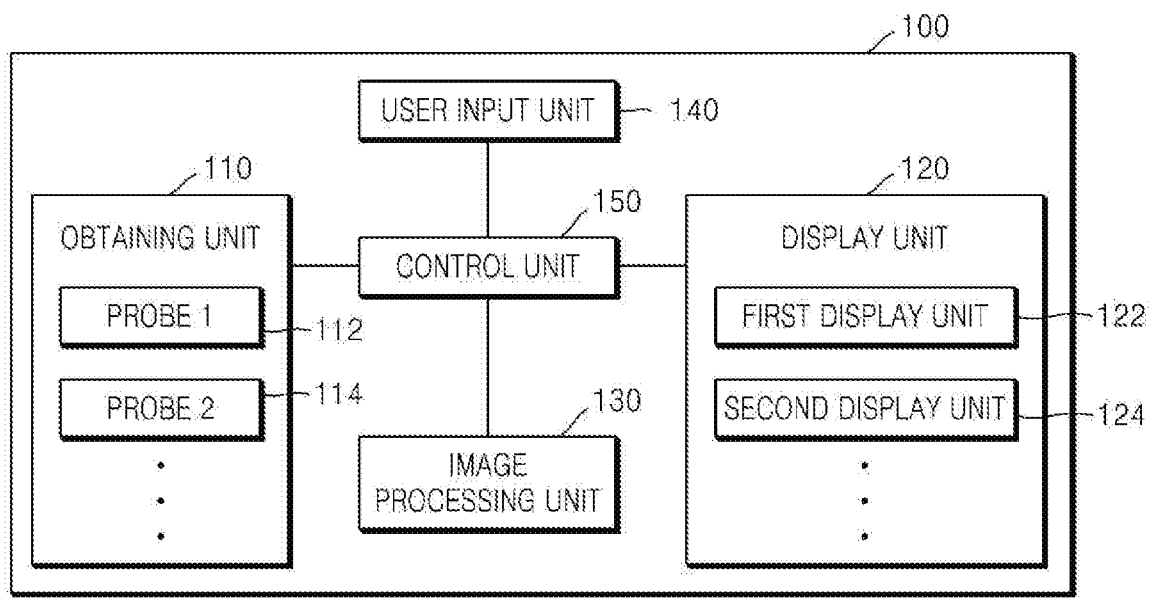
FIG. 3 is a block diagram illustrating a structure of the portable ultrasound apparatus, according to an embodiment of the present invention.

FIG. 3 is a block diagram illustrating a structure of the portable ultrasound apparatus 100, according to an embodiment of the present invention. In addition to the aforementioned features of the portable ultrasound apparatus 100, which are described with reference to FIGS. 1 and 2, FIGS. 3 and 4 show detailed structures of the portable ultrasound apparatus 100. In the embodiment of FIG. 3, the portable ultrasound apparatus 100 may include an obtaining unit 110, a display unit 120, an image processing unit 130, the user input unit 140, and a control unit 150. In addition to the structure shown in FIG. 3, the portable ultrasound apparatus 100 may further include general-use elements.

The portable ultrasound apparatus 100 outputs an ultrasound image that is generated by scanning a target object, and thus, the portable ultrasound apparatus 100 diagnoses the target object. That is, the portable ultrasound apparatus 100 receives an echo signal from the target object via the obtaining unit 110 including the probes 112 and 114, generates an ultrasound image from ultrasound data that is processed by the image processing unit 130, and displays the ultrasound image on the display unit 120. The portable ultrasound apparatus 100 may receive various types of user inputs via the user input unit 140 and then may control the ultrasound data or the ultrasound image.

The ultrasound image that is generated by the portable ultrasound apparatus 100 may include not only a two-dimensional (2D) image showing a cross-section of the target object but may also include three-dimensional (3D) volume data. Also, the portable ultrasound apparatus 100 may generate not only the ultrasound image in a gray scale that is obtained by scanning the target object according to an amplitude mode (hereinafter, the A mode), a brightness mode (hereinafter, the B mode), and a motion mode (hereinafter, the M mode) but may also generate a Doppler image showing movement of the target object, by using colour information in Doppler data. The Doppler image generated by the portable ultrasound apparatus 100 may include at least one of a blood flow Doppler image (also called 'colour Doppler image') showing blood flow and a tissue Doppler image showing movement of tissue.

The obtaining unit 110 obtains the ultrasound data of the target object. That is, as described above, the obtaining unit 110 may scan the target object and may obtain the ultrasound data based on an echo signal that is received from the target object. In more detail, as illustrated in FIG. 3, the obtaining unit 110 may transmit an ultrasound signal to the target object by bringing the probes 112 and 114 close to the target object, and may obtain the ultrasound data from the echo signal that is to be received from the target object.

The obtaining unit 110 may include at least two probes, each having one of various transducers including a phased array-type transducer, an annular array-type transducer, or the like, as well as the linear array-type transducer and the convex-array type transducer that are shown in FIGS. 1 and 2.

Also, while the obtaining unit 110 includes probes having the same type of transducers, specifications of the probes may differ. For example, when the obtaining unit 110 includes two probes both having convex array-type transducers, specifications, such as a frequency of an ultrasound signal to be transmitted, a bandwidth, a total number of channels of a transducer, the resolution of a probe, or the like of the two probes may differ.

The obtaining unit 110 may include the at least two probes 112 and 114, as described above, and a transducer included in each of the probes 112 and 114 may be formed of a plurality of elements (or channels). In the present embodiment, each of the probes 112 and 114 may randomly set an order by which the plurality of elements transmit an ultrasound signal. That is, the ultrasound signal may be transmitted from a first element or a last element from among the plurality of elements in each of the probes 112 and 114, and the order of transmitting the ultrasound single may not be fixed to a predetermined direction and order but may be changed via a setting operation.

For example, when each of the probes 112 and 114 includes a transducer formed of 128 elements, each of the probes 112 and 114 may transmit an ultrasound signal from a first element or a $128^{th}$ element. That is, each of the probes 112 and 114 may transmit the ultrasound signal according to an order from the first element to the $128^{th}$ element or from the $128^{th}$ element to the first element. Accordingly, while a user holds the probes 112 and 114 and scans the target object, if the user switches the hand that holds the probes 112 and 114, or holds the probes 112 and 114 upside down, the probes 112 and 114 may change a direction of transmitting an ultrasound signal. Thus, the user may not need to constantly check a direction in which the user holds the probes 112 and 114, so that user convenience in a diagnosis may be improved.

The obtaining unit 110 may directly obtain the ultrasound data from the target object and may receive ultrasound data from an external device. That is, the obtaining unit 110 may receive the ultrasound data via a wired or wireless network. For example, although not illustrated in FIG. 3, the obtaining unit 110 may include a short distance communication module, a mobile communication module, a wireless Internet module, or the like, and may receive the ultrasound data from the external device or a server by using at least one of the aforementioned modules.

The short distance communication module indicates a module for short distance communication. Examples of the short distance communication may include, but are not limited to, Wi-Fi, Bluetooth, Bluetooth Low Energy (BLE), ultra-wide band (UWB), ZigBee, near field communication (NFC), Wi-Fi Direct (WFD), and infrared Data Association (IrDA).

The mobile communication module exchanges a wireless signal with at least one of a base station in a mobile communication network, the external device, and the server. The mobile communication module is for accessing wireless Internet. The wireless Internet module may be embedded in the portable ultrasound apparatus 100 or may be arranged outside the portable ultrasound apparatus 100.

Also, the obtaining unit 110 may receive various types of data, such as an ultrasound image, and Doppler data related to the ultrasound image from another device or a cloud server in a hospital server via a picture archiving and communication system (PACS).

The display unit 120 may display and output information that is processed by the portable ultrasound apparatus 100. For example, the display unit 120 may display the ultrasound image of the target object on a screen of the portable ultrasound apparatus 100 or may display a user interface (UI) or a graphic UI (GUI) related to function setting. Also, the display unit 120 may display the control screen for a control of the ultrasound data or the ultrasound image.

When the display unit 120 and a touch pad to be described later form a mutual layer structure and thus are formed as a touch screen, the display unit 120 may be used as both an output device and an input device. The display unit 120 may include at least one of a liquid crystal display (LCD), a thin film transistor-liquid crystal display (TFT-LCD), an organic light-emitting display device, a flexible display, a three-dimensional (3D) display, and an electrophoretic display. In another embodiment, the portable ultrasound apparatus 100 may include at least two display units 120.

The image processing unit 130 generates various types of ultrasound images by processing the ultrasound data obtained by the obtaining unit 110. That is, the image processing unit 130 may generate ultrasound images according to the A mode, B mode, and C mode, and may generate not only a cross-sectional image but may also generate a 3D ultrasound image using volume data. Further, the image processing unit 130 may also generate a Doppler image by using Doppler data.

Further, the image processing unit 130 may generate the control screen so as to control the ultrasound image or the ultrasound data. That is, the image processing unit 130 may generate the control screen to be displayed on the display unit 120, by using the GUI or various graphic effects. Also, the image processing unit 130 may generate the various graphic effects, such as icons, menu lists, text, or thumbnails, which are matched with functions to control the ultrasound image or the ultrasound data.

The user input unit 140 indicates a means by which a user inputs data so as to control the portable ultrasound apparatus 100. For example, the user input unit 140 may be formed of, but is not limited to, buttons, a key pad, a dome switch, a touch pad (a touch capacitive type touch pad, a pressure resistive type touch pad, an infrared beam sensing type touch pad, a surface acoustic wave type touch pad, an integral strain gauge type touch pad, a piezoelectric effect type touch pad, or the like), a jog wheel, a jog switch, or the like. The plurality of buttons that are shown in the left-side view and the right-side view of FIG. 2 may be an example of the user input unit 140.

In particular, as described above, when the touch pad and the display unit 120 form the mutual layer structure, this structure may be referred to as a touch screen. The touch screen may detect not only an actual touch but may also detect a proximate touch. In the present embodiment, the actual touch means a case in which a pointer actually touches the touch screen, and the proximate touch means a case in which the pointer does not actually touch the touch screen but approaches the touch screen by a predetermined distance. In the present embodiment, the pointer indicates a tool to actually touch or proximately touch a predetermined portion of a displayed screen. An example of the tool includes a stylus pen, a finger of the user, or the like. Although not illustrated, in order to detect the actual touch or the proximate touch on the touch screen, the touch screen may internally or externally have various sensors. An example of the sensor to detect the actual touch or the proximate touch on the touch screen may include a tactile sensor. The tactile sensor detects a contact of a specific object by at least as much as a person can detect. The tactile sensor may detect various types of information, such as the roughness of a contact surface, the hardness of the contact object, the temperature of a contact point, or the like.

Also, another example of the sensor to detect the actual touch or the proximate touch on the touch screen may include a proximity sensor. The proximity sensor detects the existence of an object that approaches a predetermined detection surface or that exists nearby, by using a force of an electro-magnetic field or infrared rays, without using a mechanical contact. Examples of the proximity sensor include a transmission-type photoelectric sensor, a direction reflection-type photoelectric sensor, a mirror reflection-type photoelectric sensor, a high frequency oscillation-type proximity sensor, a capacity-type proximity sensor, a magnetic proximity sensor, an infrared-type proximity sensor, or the like.

The user input that is received by the user input unit 140 may be various ones. For example, the user input unit 140 may include various types of user input including a tap input, a touch & hold input, a drag input, a drag & drop input, a flick input, a pinching input, or the like.

When the user input unit 140 includes a plurality of buttons, each of the plurality of buttons may be matched with various functions to control the portable ultrasound apparatus 100. Here, the functions of the buttons may be previously matched with default values, respectively, and may be changed according to settings by the user. That is, for user convenience, the user may match user-desired functions with the buttons, respectively, so that convenience of user manipulation of the portable ultrasound apparatus 100 may be improved.

The control unit 150 controls elements included in the portable ultrasound apparatus 100. For example, the control unit 150 may transmit the ultrasound data that is obtained by the obtaining unit 110 and then may control the image processing unit 130 to generate the ultrasound image, or may control the display unit 120 to display the ultrasound image that is generated by the image processing unit 130.

Figure 4:
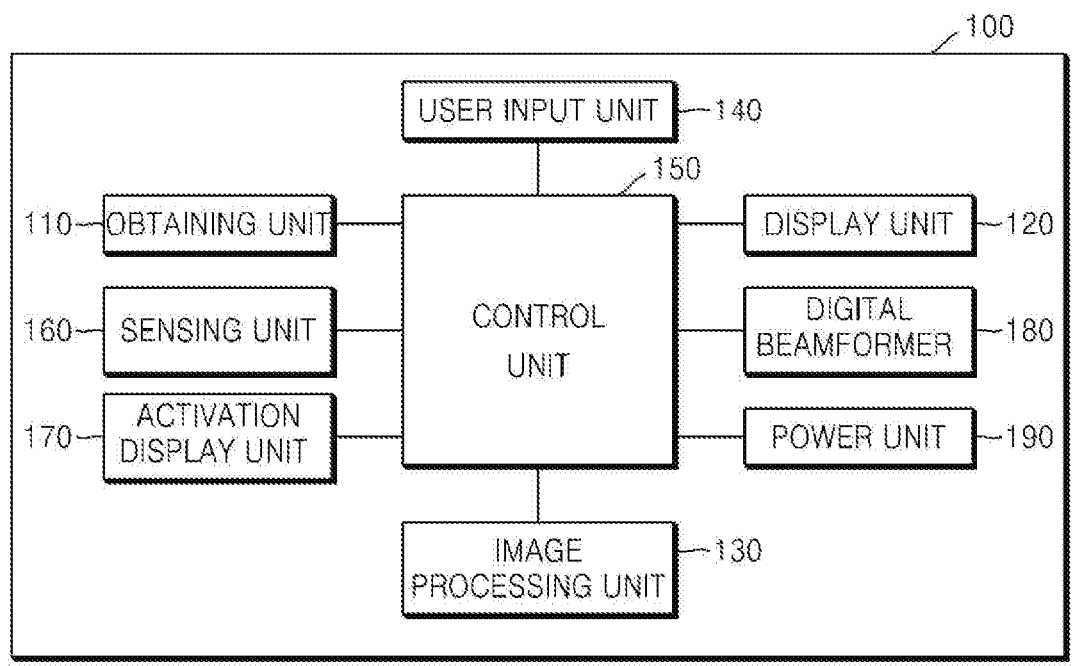
FIG. 4 is a block diagram illustrating a structure of the portable ultrasound apparatus, according to another embodiment of the present invention.

FIG. 4 is a block diagram illustrating a structure of the portable ultrasound apparatus 100, according to another embodiment of the present invention. In the embodiment of FIG. 4, the portable ultrasound apparatus 100 further includes elements, as well as the elements that are described with reference to FIG. 3. In this regard, detailed descriptions, which are the same as the aforementioned ones of FIG. 3, are omitted.

In the present embodiment, the portable ultrasound apparatus 100 may further include a sensing unit 160, the activation display unit 170, a digital beamformer 180, and a power unit 190, as well as the obtaining unit 110, the display unit 120, the image processing unit 130, and the control unit 150 that are described with reference to FIG. 3. However, the structure of the portable ultrasound apparatus 100 is not limited to the elements shown in FIG. 4, and thus, the portable ultrasound apparatus 100 may further include other elements as well as the aforementioned elements. Also, the portable ultrasound apparatus 100 may further include elements other than the aforementioned elements and then may form a portable ultrasound system.

The sensing unit 160 detects an activated probe. That is, the sensing unit 160 detects, among at least two probes included in the obtaining unit 110, a currently-activated probe that is to scan a target object. In more detail, one probe from among the at least two probes included in the portable ultrasound apparatus 100 may transmit an ultrasound signal to the target object, and the sensing unit 160 may detect the one probe that is currently activated.

The sensing unit 160 may detect the activated probe by using various physical/electrical methods. For example, the sensing unit 160 may detect the probe that faces in a downward direction so as to diagnose the target object, by using at least one of a gyro sensor, an acceleration sensor, a tilt sensor, and a gravity sensor. In another example, the sensing unit 160 may detect the activated probe in a manner that the sensing unit 160 recognizes which probe directly contacts the target object, by sensing an electrical signal. The sensing unit 160 may detect the activated probe by using various methods other than the aforementioned examples.

The activation display unit 170 displays the activated probe. That is, the activation display unit 170 may display the activated probe that is detected by the sensing unit 160, by using a visual effect. For example, the activation display unit 170 may include a light-emitting diode (LED) lamp around each of the at least two probes, and when the sensing unit 160 detects the activated probe, the activation display unit 170 may apply an electrical signal to the LED lamp around the activated probe. Accordingly, a user may easily recognize which probe is currently activated.

For example, referring to the left-side view and the right-side view of FIG. 2, the activation display unit 170 may be formed around each of the at least two probes, and when the activated probe is detected, the activation display unit 170 may emit light to show which one of the at least two probes is activated.

The digital beamformer 180 focuses an ultrasound signal of a probe included in the obtaining unit 110, and adjusts focusing of an echo signal. That is, the digital beamformer 180 may apply a delay time to the ultrasound signal that is transmitted by the probe and thus may focus a beam of the ultrasound signal, or may adjust dynamic focusing of the echo signal that is reflected from the target object.

The digital beamformer 180 may be formed to correspond to each of the at least two probes that are included in the obtaining unit 110. That is, the portable ultrasound apparatus 100 may include digital beamformers 180 that correspond to the at least two probes, respectively. Alternatively, in another embodiment, the portable ultrasound apparatus 100 may include one digital beamformer 180 that commonly controls the at least two probes. In other words, the digital beamformer 180 may control one corresponding probe or may commonly control the at least two probes.

The power unit 190 supplies power to the portable ultrasound apparatus 100 and the elements that are included in the portable ultrasound apparatus 100. That is, the power unit 190 may supply power to the structures shown in FIGS. 3 and 4, so as to operate the portable ultrasound apparatus 100.

The power unit 190 may be charged in a wired or wireless manner. That is, the power unit 190 may be charged by being connected to an external power source in a wired manner by using a line, or may be charged by wirelessly receiving power from an external power source. Regarding the wireless charging, the power unit 190 may be supplied the power by using various short distance power transmission methods, such as wireless charging using electromagnetic induction, wireless charging using magnetic resonance, or the like, and then may supply power to the elements included in the portable ultrasound apparatus 100.

In another embodiment, the power unit 190 may store the power received from the external power source and then may supply the power, or may supply wireless power without a charge procedure. That is, the power unit 190 may directly transmit wireless electricity (i.e., wireless power) that is received from the external power source to the elements in the portable ultrasound apparatus 100, so that the power unit 190 may operate the portable ultrasound apparatus 100. By doing so, in the present embodiment, a physical space for charging the power unit 190 may be reduced, so that a weight and volume of the portable ultrasound apparatus 100 may be decreased.

As described above, the portable ultrasound apparatus 100 may include the at least two probes having different specifications, so that the portable ultrasound apparatus 100 may efficiently diagnose the target object. Further, the portable ultrasound apparatus 100 may include at least two display units and thus may simultaneously display the ultrasound image and a control screen related to the ultrasound image. Accordingly, the user may adjust the portable ultrasound apparatus 100 so as to obtain a diagnosis result that shows the target object in a best way.

According to the portable ultrasound apparatus 100 and the portable ultrasound system, not only user convenience in a diagnosis but also the exactness and efficiency of the diagnosis may be improved.

Figure 5:
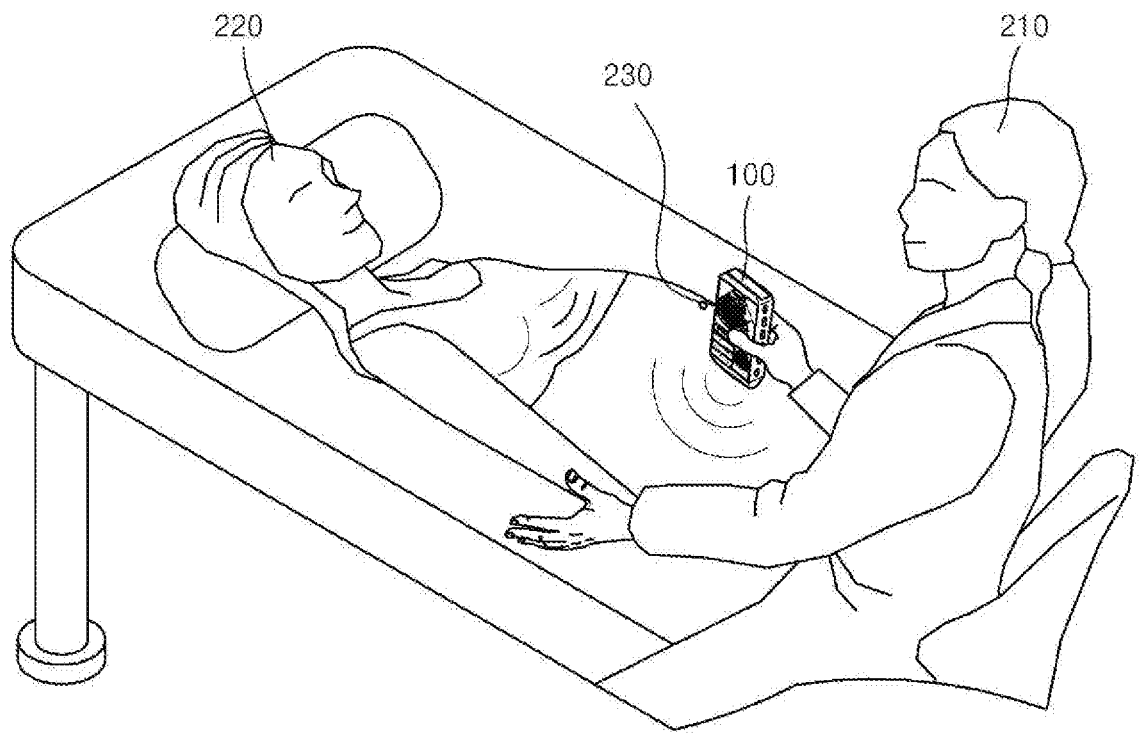
FIG. 5 illustrates an environment in which a user diagnoses a target object by using the portable ultrasound apparatus according to an embodiment of the present invention.

FIG. 5 illustrates an environment in which a user 210 diagnoses a target object 220 by using the portable ultrasound apparatus 100 according to an embodiment of the present invention.

The user 210 of the portable ultrasound apparatus 100 brings the portable ultrasound apparatus 100 close to the target object 220 and then scans the target object 220. The portable ultrasound apparatus 100 may transmit an ultrasound signal to the target object 220, may generate an ultrasound image 230 by processing a reflected echo signal, and may display the ultrasound image 230.

The user 210 of the portable ultrasound apparatus 100 may be a medical expert including, but is not limited to, a doctor, a nurse, a clinical pathologist, and a medical image expert. Also, the target object 220 may be a part of a human body and may be organs, such as the heart, the brain, the stomach, or the like, or an unborn child. However, the target object 220 is not limited to the shown part of the human body and thus may include all objects that may receive and reflect an ultrasound signal.

In an ultrasound apparatus according to the related art, a probe that transmits an ultrasound signal and a display unit are separately arranged, such that the user 210 has to operate the probe while the user 210 keeps viewing the target object 220. Since a gaze of the user 210 has to be maintained on the display unit while the user 210 moves the probe so as to diagnose the target subject 220, the efficiency in a diagnosis deteriorates.

However, in the portable ultrasound apparatus 100 according to the present embodiment, a display unit that displays the ultrasound image 230 is adjacent to the probe that transmits the ultrasound signal to the target subject 220. That is, the user 210 may adjust a position at which the probe scans the target subject 220 and may simultaneously check the ultrasound image 230. Accordingly, the user 210 of the portable ultrasound apparatus 100 may exactly diagnose the target subject 220.

FIGS. 6 through 9 illustrate examples in which the portable ultrasound apparatus 100 displays an ultrasound image and a control signal on a display unit, according to embodiments of the present invention.

Figure 6:
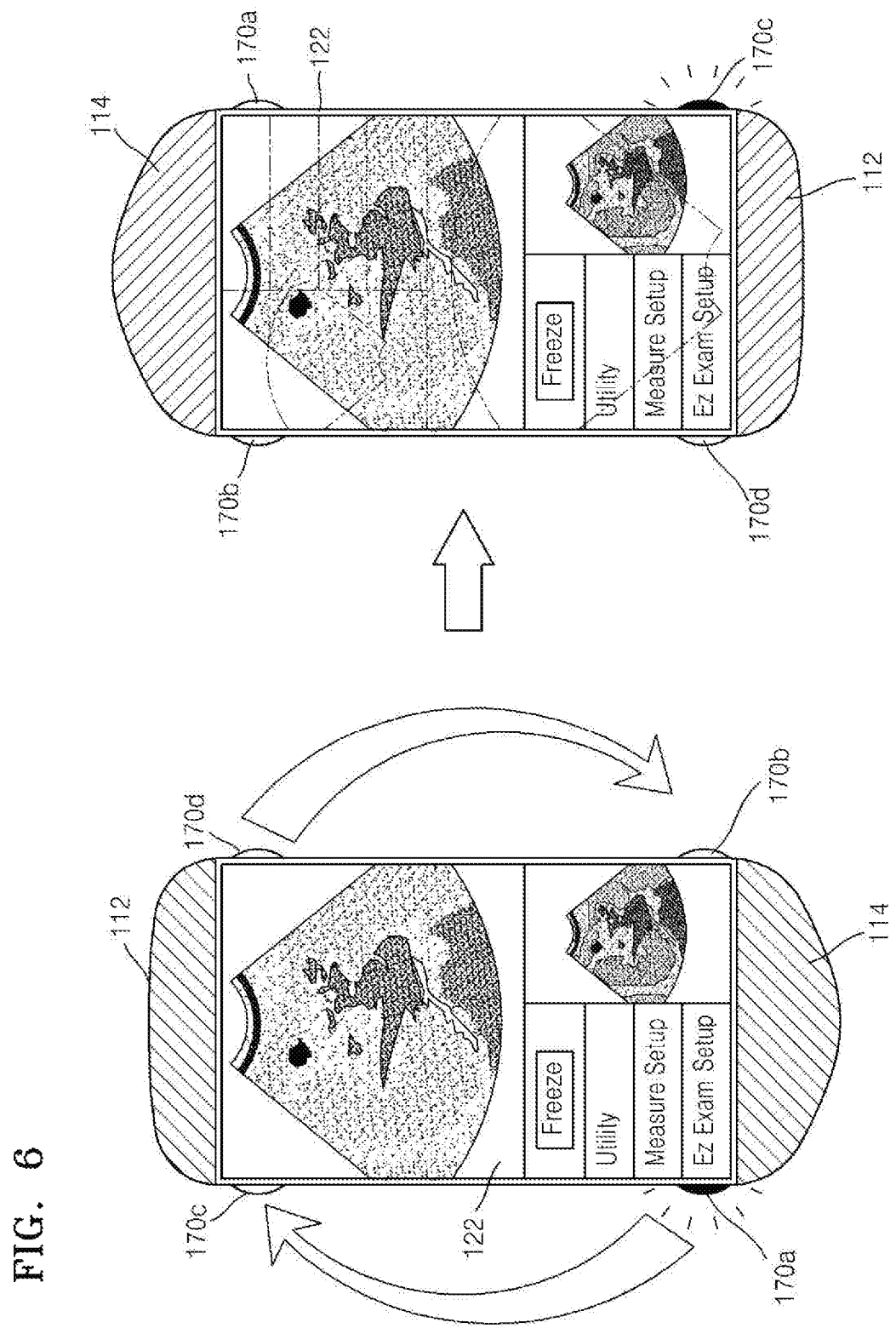
FIG. 6 illustrates an example in which a screen is rotated according to an activated probe and then is displayed, according to an embodiment of the present invention.

FIG. 6 illustrates an example in which a screen is rotated according to an activated probe and then is displayed, according to an embodiment of the present invention. As described above, the portable ultrasound apparatus 100 may include the at least two probes 112 and 114 and the at least two display units 122 and 124.

First, a left side in FIG. 6 is described. The portable ultrasound apparatus 100 displays an ultrasound image of a scanned target object on the display unit 122 (also referred to as the first display unit 122). The portable ultrasound apparatus 100 scans the target object by using, from among two probes 112 and 114, the probe 114 that includes the convex array-type transducer.

As described above with reference to FIG. 4, the portable ultrasound apparatus 100 may detect the activated probe 114 that scans the target object. In order to detect the activated probe 114, as described with reference to FIG. 4, the portable ultrasound apparatus 100 may use a physical sensor, such as the gyro sensor, the acceleration sensor, the tilt sensor, or the gravity sensor, or may use an electrical signal.

Also, in order to show the activated probe 114 to a user, the portable ultrasound apparatus 100 may turn on or may flicker out an activation display unit 170a that is arranged adjacent to the activated probe 114. The fact that only the activation display unit 170a from among activation display units 170a and 170b that correspond to the probe 114 is turned on may indicate a direction in which an ultrasound signal is transmitted from the probe 114.

In more detail, as described above with reference to FIG. 3, the portable ultrasound apparatus 100 may transmit the ultrasound signal from a first element or a last element from among the plurality of elements of the probe 114. Accordingly, the portable ultrasound apparatus 100 may turn on the activation display unit 170a that indicates the fact that the ultrasound signal is transmitted from a leftmost element of the probe 114. Similarly, when the ultrasound signal is transmitted from a rightmost element of the probe 114, the portable ultrasound apparatus 100 may turn on the activation display unit 170b.

Hereinafter, a right side in FIG. 6 is described. The user of the portable ultrasound apparatus 100 scans the target object by using the probe 112 including the linear array-type transducer. That is, as illustrated in FIG. 6 by arrows, the user of the portable ultrasound apparatus 100 rotates the portable ultrasound apparatus 100 by 180 degrees and then selects the probe 112.

Accordingly, the portable ultrasound apparatus 100 recognizes that a probe to transmit an ultrasound signal is changed from the probe 114 to the probe 112, and then detects the probe 112 as an activated probe. As in the left side in FIG. 6, the portable ultrasound apparatus 100 may indicate which probe is currently activated, by turning on an activation display unit 170c or an activation display unit 170d that are formed around the activated probe 112.

The fact that the activation display unit 170c is turned on may mean that the portable ultrasound apparatus 100 leftward transmits an ultrasound signal from a rightmost element of a plurality of elements included in the probe 112. As described with reference to the left side in FIG. 6, the portable ultrasound apparatus 100 may rightward transmit the ultrasound signal from a left element of the probe 112 and may turn on the activation display unit 170d.

The portable ultrasound apparatus 100 may rotate and display the screen, based on an activated probe. That is, when the activated probe is changed from the probe 114 to the probe 112, the portable ultrasound apparatus 100 may rotate an ultrasound image that is displayed on the first display unit 122 by 180 degrees.

When the user of the portable ultrasound apparatus 100 uses the portable ultrasound apparatus 100 having the two probes 112 and 114, the user may need to rotate the portable ultrasound apparatus 100 as illustrated in FIG. 6. In this regard, the portable ultrasound apparatus 100 may detect the activated probe and may rotate and may display a screen according to the activated probe.

As shown in the embodiment of FIG. 5, the user 210 of the portable ultrasound apparatus 100 generally positions a probe in a lower direction and then scans the target object 220, and thus, the screen of the portable ultrasound apparatus 100 may be rotated so as to allow the activated probe 112 to be positioned in the lower direction as shown in the right side in FIG. 6. However, a relation between the activated probe and a direction of the displayed screen in the portable ultrasound apparatus 100 may vary according to specification and types of a probe and thus is not limited to the features of the present embodiment.

Figure 7:
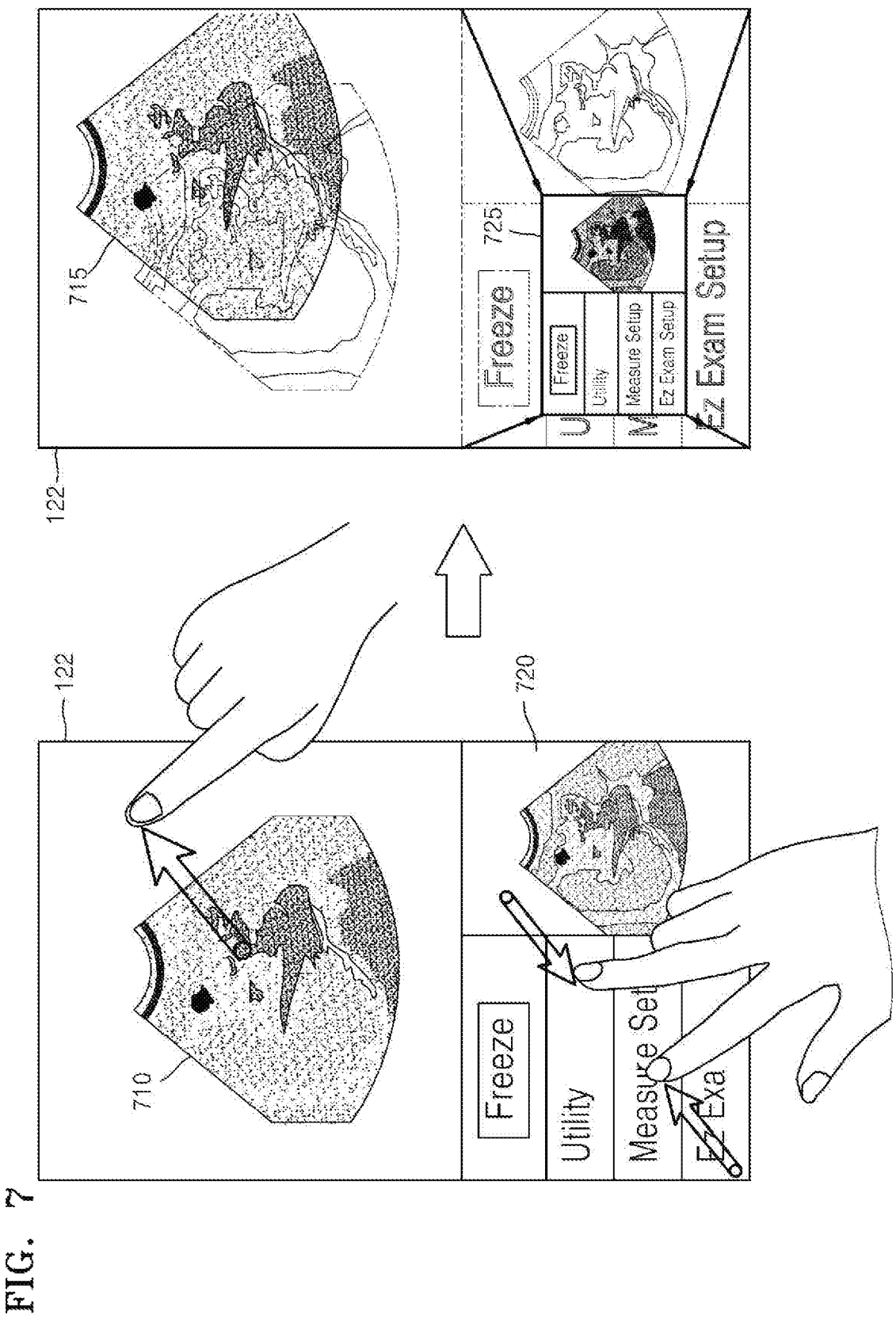
FIG. 7 illustrates an example in which a size and position of a displayed image are adjusted, according to an embodiment of the present invention.

FIG. 7 illustrates an example in which a size and position of a displayed image are adjusted, according to an embodiment of the present invention. Referring to a left picture in FIG. 7, the portable ultrasound apparatus 100 displays an ultrasound image 710 and ultrasound image-related information 720 on the first display unit 122.

The ultrasound image-related information 720 may include various types of information, such as biological information (e.g., a thickness of a target object, a length of the target object, or the like) about the target object displayed on the ultrasound image 710, content information (e.g., the resolution and size of the ultrasound image 710, the reproduction time of a moving picture, or the like) of the ultrasound image 710, or the like which are about the ultrasound image 710 and a diagnosis.

The portable ultrasound apparatus 100 may receive a user input related to dragging the ultrasound image 710 on the first display unit 122. Also, the portable ultrasound apparatus 100 receives a user input related to pinching the ultrasound image-related information 720 on the first display unit 122.

Next, referring to a right picture in FIG. 7, the portable ultrasound apparatus 100 may adjust a size and a position of an image to be displayed on the first display unit 122, based on the received user inputs. That is, the portable ultrasound apparatus 100 may move the ultrasound image 710 to a position 715 based on the user input related to the dragging and then may display the ultrasound image 710. Also, the portable ultrasound apparatus 100 may decrease a size of the ultrasound image-related information 720 to a size 725 based on the user input related to the pinching and may display the ultrasound image-related information 720.

That is, the portable ultrasound apparatus 100 may adjust a size and a position of an image and a screen displayed on the display units 122 and/or 124.

Accordingly, a user may freely dispose a screen for a display by the portable ultrasound apparatus 100, so that a user-desired screen composition may be possible. Thus, the user may efficiently diagnose the target object by using a menu that the user mainly uses or by using a user-familiar interface.

However, a relation between the user inputs and the adjustment of the size and the position of the image, which is described above with reference to FIG. 7, is an example for convenience of description. That is, various types of user inputs may match with functions related to adjusting the size and the position of the image, and matching relations may be changed according to user settings.

Figure 8:
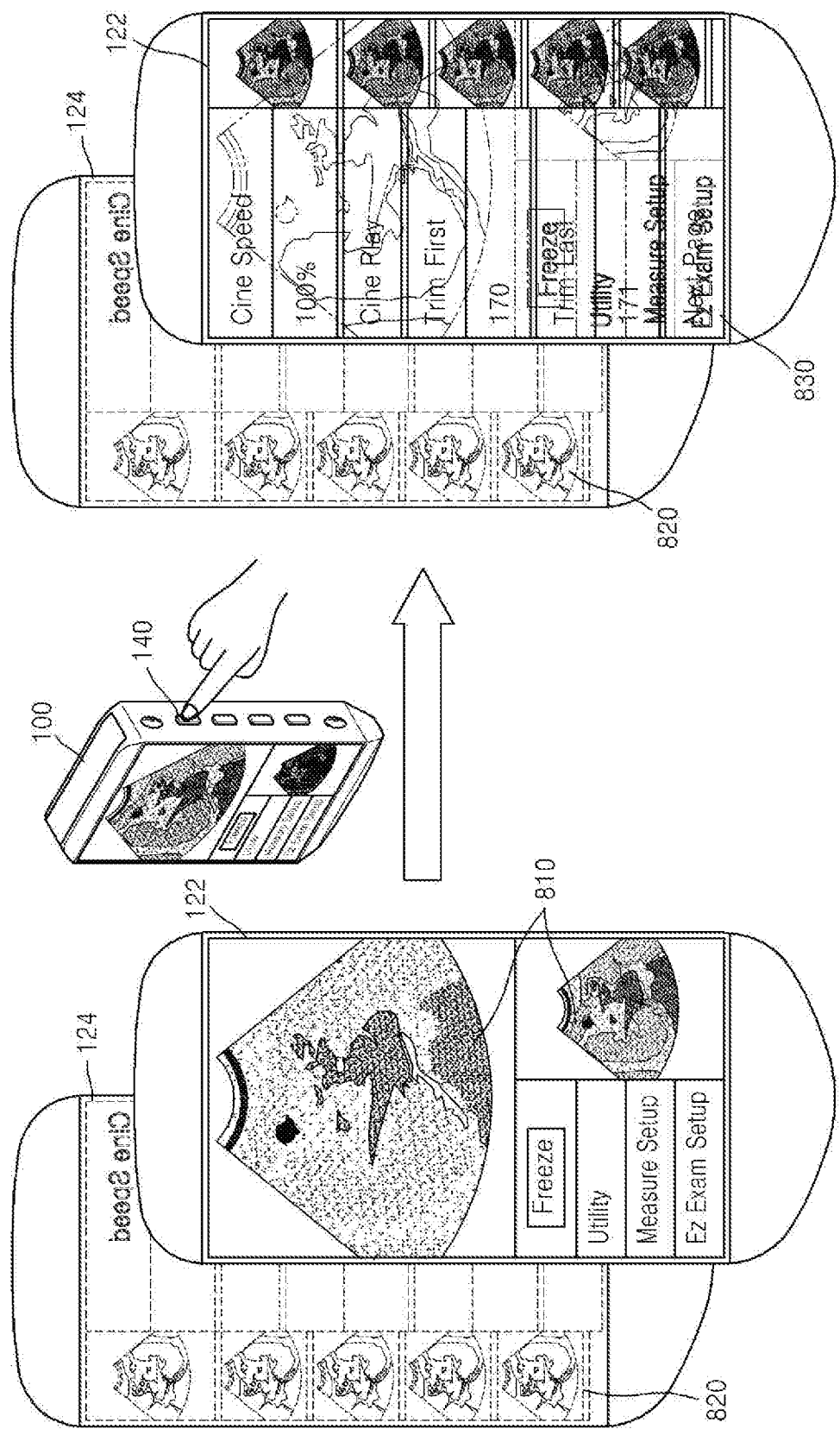
FIG. 8 illustrates an example in which an image that is displayed on a display unit is displayed on another display unit based on a user input, according to an embodiment of the present invention.

FIG. 8 illustrates an example in which an image that is displayed on a display unit is displayed on another display unit based on a user input, according to an embodiment of the present invention.

Referring to a left picture in FIG. 8, the portable ultrasound apparatus 100 displays an ultrasound image and related information 810 on the first display unit 122. Also, the portable ultrasound apparatus 100 displays a control screen 820 on the second display unit 124 so as to control ultrasound data and the ultrasound image.

Then, referring to a middle picture in FIG. 8, the portable ultrasound apparatus 100 receives a user input related to pressing one of a plurality of buttons included in the user input unit 140. In this regard, the user input related to pressing the button may be an example, thus, a display unit of the portable ultrasound apparatus 100 may be touched or the portable ultrasound apparatus 100 may receive the user input via another element other than the button.

Referring to a right picture in FIG. 8, the portable ultrasound apparatus 100 displays the control screen 820, which is displayed on the second display unit 124, on the first display unit 122 (refer to reference numeral 830). The portable ultrasound apparatus 100 may overlap and display the control screen 820 on the first display unit 122, or the control screen 820 in the form of a pop-up screen may be displayed on the first display unit 122. Alternatively, the portable ultrasound apparatus 100 may dim and display the ultrasound image and related information 810 by adjusting the brightness of the ultrasound image and related information 810 that are displayed on the first display unit 122, and may overlap and brightly display the control screen 820 on the ultrasound image and related information 810 that are dimmed.

That is, when the user wants to check the control screen 820 while the portable ultrasound apparatus 100 scans a target object, if the user turns the portable ultrasound apparatus 100 upside down so as to check the second display unit 124, a discontinuous change occurs in the ultrasound data and the ultrasound image. Accordingly, the portable ultrasound apparatus 100 may display the control screen 820, which is displayed on the second display unit 124, on the first display unit 122 (refer to reference numeral 830), based on the user input related to a screen switch. As a result, the user may easily check content that is displayed on a rear surface, without moving or turning the portable ultrasound apparatus 100 upside down.

The example shown in FIG. 8 is also applied to an opposite case. That is, when the portable ultrasound apparatus 100 receives a user input related to a screen switch while the portable ultrasound apparatus 100 displays the control screen 820 on the second display unit 124, the portable ultrasound apparatus 100 may display the ultrasound image and related information 810, which are displayed on the first display unit 122, on the second display unit 124.

The first display unit 122 and the second display unit 124 may have the same size and may be disposed at positions that correspond to each other. For example, as illustrated in FIG. 8, the first display unit 122 and the second display unit 124 may be disposed to face each other at the same positions on both surfaces of the portable ultrasound apparatus 100. Accordingly, the user of the portable ultrasound apparatus 100 may conveniently manipulate at least two display units of the portable ultrasound apparatus 100.

Figure 9:
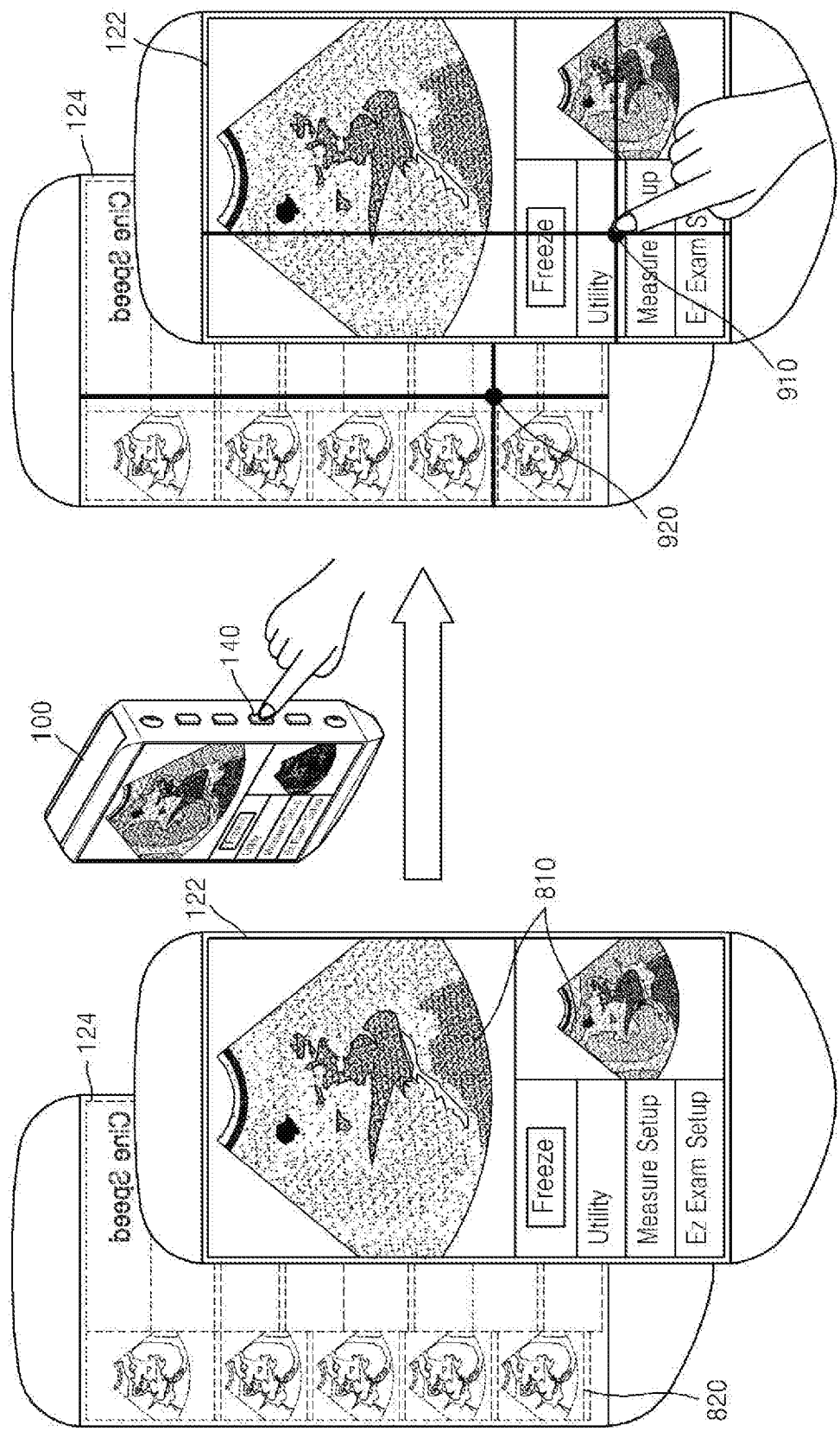
FIG. 9 illustrates an example in which a position on another display unit is detected, based on a user input with respect to a corresponding position on a display unit, according to an embodiment of the present invention.

FIG. 9 illustrates an example in which a position on another display unit is detected, based on a user input with respect to a corresponding position on a display unit, according to an embodiment of the present invention.

Referring to a left picture in FIG. 9, the portable ultrasound apparatus 100 displays the ultrasound image and related information 810 on the first display unit 122, and displays the control screen 820 on the second display unit 124.

Then, referring to a middle picture in FIG. 9, the portable ultrasound apparatus 100 receives a user input of selecting a position on a display unit at an opposite side via the user input unit 140. For example, as illustrated in the middle picture in FIG. 9, the portable ultrasound apparatus 100 may receive a user input of pressing one of the buttons that are arranged at a side surface of the portable ultrasound apparatus 100.

Referring to a right picture in FIG. 9, the portable ultrasound apparatus 100 receives a user input of touching a position on the first display unit 122. That is, the portable ultrasound apparatus 100 receives a user input of selecting a position 910. As described above with reference to the middle picture in FIG. 9, according to the embodiment involving selecting the position on the display unit at the opposite side, when the portable ultrasound apparatus 100 receives the user input of selecting the position 910, the portable ultrasound apparatus 100 may select a position 920 on the second display unit 124 which corresponds to the position 910.

In more detail, coordinates of the first display unit 122 previously match with coordinates of the second display unit 124. That is, the portable ultrasound apparatus 100 previously matches the coordinates of the first display unit 122 with the coordinates of the second display unit 124 and stores them, so that the portable ultrasound apparatus 100 matches a position on the first display unit 122 with a position on the second display unit 124. Accordingly, when the portable ultrasound apparatus 100 detects a user input of selecting the position 910 on the first display unit 122, the portable ultrasound apparatus 100 may select the position 920 on the second display unit 124.

That is, according to the embodiment of FIG. 8, the portable ultrasound apparatus 100 displays the screen, which is displayed on the second display unit 124, on the first display unit 122, so that the portable ultrasound apparatus 100 provides a screen to the user that is invisible to the user and is displayed on a display unit at an opposite side. Unlike the embodiment of FIG. 8, according to the embodiment of FIG. 9, the portable ultrasound apparatus 100 selects a position on the second display unit 124 based on a user input of touching a position on the first display unit 122. Accordingly, the portable ultrasound apparatus 100 may execute a function provided by another display unit at the opposite side, not a display unit that currently provides information to the user, so that the convenience of user manipulation of the portable ultrasound apparatus 100 may be improved.

However, the features of the embodiment of FIG. 9 may also be applied to an opposite case. That is, based on a user input of selecting a position on the second display unit 124, the portable ultrasound apparatus 100 may select a position on the first display unit 122 which corresponds to the selected position.

Figure 10:
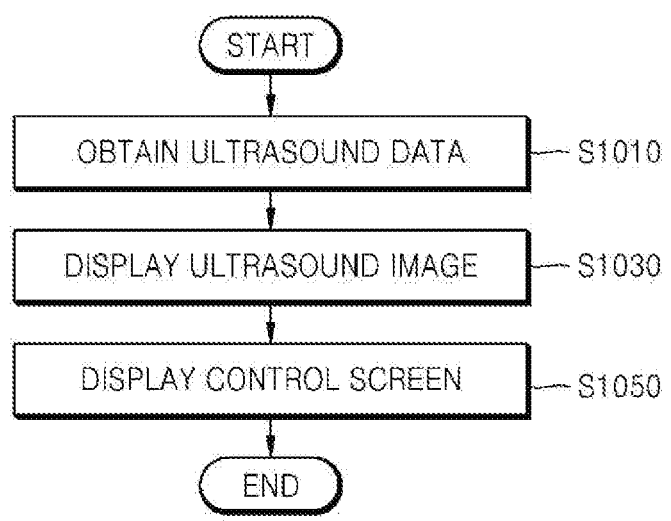
FIG. 10 is a flowchart of an ultrasound diagnosis method performed by using the portable ultrasound apparatus, according to an embodiment of the present invention.

Hereinafter, a method of performing an ultrasound diagnosis by using elements included in the portable ultrasound apparatus 100 will now be described. FIG. 10 is a flowchart of an ultrasound diagnosis method performed by using the portable ultrasound apparatus 100, according to an embodiment of the present invention.

The flowchart of FIG. 10 is formed of operations that are processed in chronological order by the portable ultrasound apparatus 100, the obtaining unit 110, the display unit 120, the image processing unit 130, the user input unit 140, and the control unit 150 that are illustrated in FIGS. 3 and 4.

Thus, hereinafter, although descriptions are omitted, if the descriptions are provided above with reference to FIGS. 3 and 4, the descriptions may also be applied to the flowchart of FIG. 10.

In operation S1010, the portable ultrasound apparatus 100 obtains ultrasound data. That is, the portable ultrasound apparatus 100 scans a target object by using a probe and then obtains ultrasound data from the target object. The portable ultrasound apparatus 100 may obtain the ultrasound data from the target object by using one of at least two different probes.

In operation S1030, the portable ultrasound apparatus 100 displays an ultrasound image. That is, the portable ultrasound apparatus 100 generates the ultrasound image based on the ultrasound data obtained in operation S1010, and displays the ultrasound image on one of the two display units. The portable ultrasound apparatus 100 may display the ultrasound image along with information related to the ultrasound image.

In operation S1030, the portable ultrasound apparatus 100 may rotate the ultrasound image based on a user input or may adjust a size or a position of the ultrasound image. Also, the portable ultrasound apparatus 100 may overlap and display a control screen on the display unit that displays the ultrasound image, wherein the control screen controls at least one of the ultrasound data and the ultrasound image.

In operation S1050, the portable ultrasound apparatus 100 displays the control screen. That is, the portable ultrasound apparatus 100 may display a GUI on a display unit that is different from the display unit in operation S1030, wherein the GUI displays several matched functions capable of controlling the ultrasound data and the ultrasound image related to an ultrasound diagnosis.

In operation S1050, as in operation S1030, the portable ultrasound apparatus 100 may rotate the control screen or may adjust a size or a position of the control screen and may display the control screen. Also, the portable ultrasound apparatus 100 may overlap and display the ultrasound image, which is displayed on the display unit in operation S1030, on the control screen, based on a user input.

According to the one or more embodiments of the present invention, the portable ultrasound apparatus 100 may include at least two probes having different specifications and thus may efficiently diagnose the target object. Further, the portable ultrasound apparatus 100 may include at least two display units and thus may display the ultrasound image and may simultaneously display the control screen related to the ultrasound image. Accordingly, a user may adjust the portable ultrasound apparatus 100 so as to obtain a diagnosis result that shows the target object well.

According to the portable ultrasound apparatus 100 and the portable ultrasound system, not only user convenience in an ultrasound diagnosis but also the exactness and efficiency of the ultrasound diagnosis may be improved While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for displaying an ultrasound image using a portable ultrasound displaying apparatus comprising at least two probes having respective specifications different from each other, the method comprising:
sensing a physical status or an electrical status of the at least two probes with respect to an object;
recognizing one of the at least two probes as a currently-activated probe based on a sensing result of the physical status or the electrical status;
transmitting ultrasound signals to the object and receiving echo signals corresponding to the ultrasound signals using the recognized probe;
generating the ultrasound image based on the echo signals; and
displaying the ultrasound image on at least one display unit,
wherein the currently-activated probe is a probe that faces in a downward direction or a probe that directly contacts the object.

2. The method of claim 1, wherein the transmitting and receiving comprises transmitting the ultrasound signals to the object and receiving the echo signals using a first probe which is activated among the at least two probes.

3. The method of claim 2, further comprising:
changing activation from the first probe to a second probe among the at least two probes; and
displaying the ultrasound image based on echo signals received by the second probe.

4. The method of claim 3, wherein the changing activation comprises changing activation based on a user input for switching activation.

5. The method of claim 1, further comprising:
displaying the recognized probe among the at least two probe using activation display unit.

6. The method of claim 1, wherein the display unit comprises a first display unit and a second display unit, and
wherein the displaying the ultrasound image comprises displaying the ultrasound image on at least one among the first display unit and the second display unit.

7. The method of claim 6, wherein the displaying the ultrasound image comprises displaying the ultrasound image in the same size on the first display unit and the second display unit.

8. The method of claim 1, wherein the displaying the ultrasound image comprises displaying the ultrasound image based on a user input for adjusting at least one among position of the ultrasound image and size of the ultrasound image.

9. The method of claim 1, wherein the displaying the ultrasound image comprises displaying a control screen displayed by a second display unit on a first display unit according to a user input for switching screens.

10. The method of claim 1, wherein the displaying the ultrasound image comprises displaying the ultrasound image displayed by a first display unit on a second display unit according to a user input for switching screens.

11. The method of claim 1, further comprising:
receiving a user input related to a first location on a first display unit; and
detecting a second location on a second display unit corresponding to the first location.

* * * * *